Figure 1:
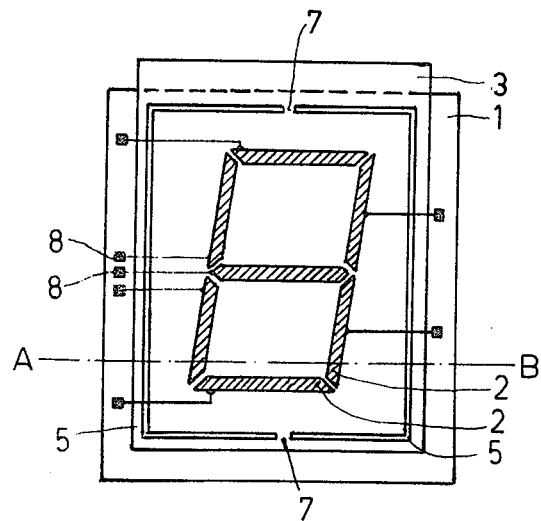

United States Patent [19]

van der Veen et al.

[11] 4,107,189

[45] Aug. 15, 1978

[54] LIQUID CRYSTALLINE COMPOUNDS

[75] Inventors: Jan van der Veen; Theodorus Cornelis Jozef Maria Hegge, both of Eindhoven, Netherlands

[73] Assignee: U.S. Philips Corporation, New York, N.Y.

[21] Appl. No.: 620,300

[22] Filed: Oct. 7, 1975

Related U.S. Application Data

[63] Continuation of Ser. No. 386,032, Aug. 6, 1973, abandoned.

[30] Foreign Application Priority Data

Aug. 18, 1972 [NL] Netherlands ............... 7211383

[51] Int. Cl.$^2$ ............................ C07C 121/70
[52] U.S. Cl. .................... 260/404; 260/465 D; 260/465 F; 260/465 K; 252/299; 350/350
[58] Field of Search ........... 260/465 D, 465 F, 465 K, 260/404

[56] References Cited

U.S. PATENT DOCUMENTS

| | | | |
|---|---|---|---|
| 2,666,789 | 1/1954 | Rorig | 260/465 X |
| 2,815,363 | 12/1957 | Rorig | 260/465 |

OTHER PUBLICATIONS

Buii-Hoë et al., Chemical Abstracts, vol. 44, 10935, (1950).
Buii-Hoë et al., Chemical Abstracts, vol. 51, 14706–14707, (1957).
Csuros et al., Chemical Abstracts, vol. 58, 7863, (1963).

*Primary Examiner*—Dolph H. Torrence
*Attorney, Agent, or Firm*—Frank R. Trifari; Norman N. Spain

[57] ABSTRACT

Liquid crystalline 2,3-diphenyl acrylonitrile derivatives, i.e., 2-(p-ethoxyphenyl)-3-(p-hexyloxyphenyl) acrylonitrile, exhibit dynamic scattering in an electrical field and are useful in electro-optic displays and as solvents in E.S.R. and N.M.R. spectroscopy.

14 Claims, 2 Drawing Figures

LIQUID CRYSTALLINE COMPOUNDS

This is a continuation, of application Ser. No. 386,032, filed Aug. 6, 1973 and now abandoned.

The invention relates to novel liquid crystalline compounds of the general formula 1:

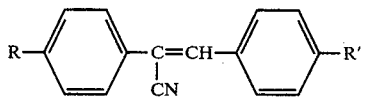

where R and R' represent a branched or unbranched alkyl group containing from 3 to 8 carbon atoms or a branched or unbranched alkoxy group containing to 8 carbon atoms or a branched or unbranched acyloxy group containing up to 10 carbon atoms, but do not both represent a methoxy group, and mixtures thereof.

The compounds are nematic liquid crystalline, colourless, thermally stable and water-resistant. In an electrical field they exhibit "dynamic scattering".

The properties of the compounds and of mixtures containing one or more of these compounds enable them to be used in displays and as solvents in E.S.R. and N.M.R. spectroscopy.

Hence, the invention also relates to a display provided with a transparent wall portion, at least two electrodes and a liquid crystalline material, characterized in that the liquid crystalline material comprises at least one or more of the compounds of the formula 1.

The compounds and their mixtures can be prepared by methods which are known for the preparation of this type of compounds and by methods which are analogous thereto.

The compounds may for example be obtained by condensation of a compound of the formula 2

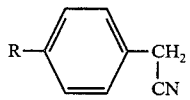

or a mixture thereof with a compound of the formula 3

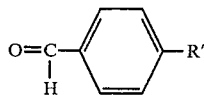

or a mixture thereof, in which formulas R and R' have the same meaning as in formula 1.

The reaction is carried out under the influence of a base, such as KOH, $NaOC_2H_5$, diethyl amine, piperidine and the like, preferably in an inert solvent, such as for example alcohols, for example, methanol, ethanol and the like and mixtures thereof with water.

The reaction temperature may vary from approximately 20° to 70° C, but is preferably room temperature.

Examples of compounds of the formula 1 are:
3-(p-methoxyphenyl)-; 3-(p-ethoxyphenyl)-; 3-(p-propoxyphenyl)-; 3-(p-butoxyphenyl)-; 3-(p-pentyloxyphenyl)-; 3-(p-hexyloxyphenyl)-; 3-(p-heptyloxyphenyl) and 3-(p-octyloxyphenyl)-2-(p-butoxyphenyl) acrylonitrile. 3-(p-methoxyphenyl)-; 3-(p-ethoxyphenyl)-; 3-(propoxyphenyl)-; 3-(p-butoxyphenyl)-; 3-(p-pentyloxyphenyl)-; 3-(p-hexyloxyphenyl)-; 3-(p-heptyloxyphenyl)- and 3-(p-octyloxyphenyl)-2-(p-hexyloxyphenyl) acrylonitrile. 3-(p-methoxyphenyl)-; 3-(p-ethoxyphenyl)-; 3-(p-propoxyphenyl)-; 3-(p-butoxyphenyl)-; 3-(p-pentyloxyphenyl)-; 3-(p-hexyloxyphenyl)-; 3-(p-heptyloxyphenyl)- and 3-(p-octyloxyphenyl)-2-(p-ethoxyphenyl) acrylonitrile. 3-(p-formyloxyphenyl)-; 3-(p-acetyloxyphenyl)-; 3-(propionyloxyphenyl)-; 3-(p-butyryloxyphenyl)-; 3-(p-valeryloxyphenyl)-; 3-(p-caproyloxyphenyl)-; 3-(p-heptyloxyphenyl)- and 3-(p-caproyloxyphenyl)-2-(p-butoxyphenyl) acrylonitrile. 3-(p-butoxyphenyl)-; 3-p-(hexyloxyphenyl)- and 3-(p-octyloxyphenyl)-2-(p-methoxyphenyl) acrylonitrile. 3-(p-ethoxyphenyl)-; 3-(p-butoxyphenyl)-; 3-(p-pentyloxyphenyl)-; 3-(p-hexyloxyphenyl)- and 3-(p-octyloxyphenyl)-2-(p-propylphenyl) acrylonitrile. 3-(p-methoxyphenyl)-; 3-(p-ethoxyphenyl)-; 3-(p-butoxyphenyl)-; 3-(p-hexyloxyphenyl)- and 3-(p-octyloxyphenyl)-2-(p-pentylphenyl) acrylonitrile. 3-(p-acetyloxyphenyl)-; 3-(p-propionyloxyphenyl)-; 3-(p-butyryloxyphenyl)- and 3-(p-caproyloxyphenyl)-2-(p-propylphenyl) acrylonitrile, as well as the corresponponding 2-(p-butylphenyl), 2-(p-pentylphenyl), 2-(p-hexylphenyl), 2-(p-heptylphenyl) and 2-(p-octylphenyl) acrylonitrile derivatives.

The invention may be illustrated by the following examples:

1. 2-(p-ethoxyphenyl)-3-(p-hexyloxyphenyl) acrylonitrile 2 g of KOH were dissolved in 30 ml of methanol whilst being heated. The solution was cooled down to room temperature, after which 3.3 g of p-ethoxybenzylcyanide and 4 g of p-hexyloxybenzaldehyde were added. The mixture was stirred and subsequently stored at room temperature for 1 hour and then at −25° C for 2 hours. The crystallisate was filtered off and subsequently recrystallized from methanol and petroleum ether (60–80). Melting point 53.5°–54° C. Transition point nematic-isotropic 80° C. In a similar way the following compounds were obtained:

| R | R' | Melting point ° C | Transition point ° C nematic-isotropic |
|---|---|---|---|
| $CH_3O$ | $C_5H_{11}O$ | 59–59.5 | 61 |
| $CH_3O$ | $C_6H_{13}O$ | 59–59.5 | 71 |
| $C_2H_5O$ | $C_4H_9$ | 41–42 | 18 |
| $CH_3O$ | $C_7H_{15}$ | 67–68 | 68 |
| $CH_3O$ | $C_8H_{17}$ | 68–69 | 73 |
| $C_4H_9O$ | $C_3H_7$ | 53.5–54.5 | 35 |
| $C_4H_9O$ | $C_6H_{13}$ | 38–39 | 40 |
| $C_4H_9O$ | $OC_5H_{11}$ | 46–47 | 70 |
| $C_4H_9O$ | $OC_6H_{13}$ | 55–56 | 77 |
| $C_9H_{19}CO_2$ | $OCH_3$ | 64.5–66 | 80 |
| $C_5H_{11}CO_2$ | $OC_4H_9$ | 56–58 | 85 |
| $C_9H_{19}CO_2$ | $OC_4H_9$ | 72–73 | 87 |

2. Compounds of the formula 1 may for example be used in a display in the following manner.

Figure 2:
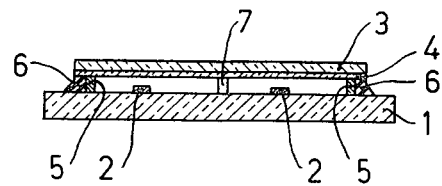

FIG. 1 shows a top-plan view of the display, FIG. 2 a sectional view taken on A-B.

A glass plate measuring 60 × 65 × 2 mm (1 in FIGS. 1 and 2) provided with an 8-shaped pattern of indium oxide (thickness 0.1 μ) consisting of seven segments 2 and a second glass plate of 50 × 60 × 1 mm 3 covered with a layer of tin oxide 4 having a thickness of 0.1 μ were cemented to each other with an epoxy glue 6 after insertion of two strips of polythene of 20 μ thickness 5, leaving the filling apertures 7 open. The space between the glass plates was subsequently filled with 2-(p-methylphenyl)-3-(p-pentyloxyphenyl) acrylonitrile via an aperture 7. Subsequently, the apertures 7 were closed with the glue.

Current supply leads are connected to the connection points 8, consisting of indium oxide and to the part of the glass plate 3 which protruded from glass plate 1.

Across glass plate 3 and the segments of glass plate 1 an alternating voltage of 25 V, 50 Hz was applied. Thus, an 8-shaped image was obtained, consisting of 7 lines which diffused the incident light against a transparent background.

What is claimed is:

1. A compound of the formula 1

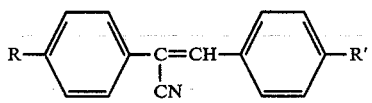

wherein R and R'are each independently moieties selected from the group consisting of alkyl of 3 to 8 carbon atoms, alkoxy of up to 8 carbon atoms and acyloxy wherein the acyl moiety is derived from an aliphatic carobxylic acid of up to 10 carbon atoms with the proviso that at least one of R and R' is other than methoxy.

2. The 2-(p-ethoxyphenyl)-3-(p-butylphenyl)acrylonitrile of claim 1.

3. The 2-(p-ethoxyphenyl)-3-(p-hexyloxyphenyl) acrylonitrile of claim 1.

4. The 2-(p-methoxyphenyl)-3-(p-pentyloxyphenyl) acrylonitrile of claim 1.

5. The 2-(p-methoxyphenyl)-3-(p-hexyloxyphenyl) acrylonitrile of claim 1.

6. The 2-(p-methoxyphenyl)-3-(p-heptylphenyl) acrylonitrile of claim 1.

7. The 2-(p-methoxyphenyl)-3-(p-octylphenyl) acrylonitrile of claim 1.

8. The 2-(p-butoxyphenyl)-3-(p-propylphenyl) acrylonitrile of claim 1.

9. The 2-(p-butoxyphenyl)-3-(p-hexylphenyl) acrylonitrile of claim 1.

10. The 2-(p-butoxyphenyl)-3-(p-pentyloxyphenyl) acrylonitrile of claim 1.

11. The 2-(p-butoxyphenyl)-3-(p-hexyloxyphenyl) acrylonitrile of claim 1.

12. The 2-(p-decanoyloxyphenyl)-3-(p-methoxyphenyl)-acrylonitrile of claim 1.

13. The 2-(p-hexanoyloxyphenyl)-2-(p-butoxyphenyl) acrylonitrile of claim 1.

14. The 2-(p-decanoyloxyphenyl)-3-(p-butoxyphenyl) acrylonitrile of claim 1.

* * * * *